(12) United States Patent
Bruun et al.

(10) Patent No.: US 7,753,945 B2
(45) Date of Patent: *Jul. 13, 2010

(54) DEPLOYMENT SYSTEM FOR AN ENDOLUMINAL DEVICE

(75) Inventors: Steven R. Bruun, Flagstaff, AZ (US);
Edward H. Cully, Flagstaff, AZ (US);
James W. Mann, Elkton, MD (US);
Mark J. Ulm, Flagstaff, AZ (US);
Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 1490 days.

This patent is subject to a terminal disclaimer.

(21) Appl. No.: 10/637,986

(22) Filed: Aug. 8, 2003

(65) Prior Publication Data
US 2004/0143315 A1 Jul. 22, 2004

Related U.S. Application Data

(63) Continuation-in-part of application No. 10/346,598, filed on Jan. 17, 2003, now Pat. No. 7,198,636.

(51) Int. Cl.
*A61F 2/06* (2006.01)
*A61F 11/00* (2006.01)
(52) U.S. Cl. ...................... 623/1.11; 606/108
(58) Field of Classification Search ............... 623/1.11; 606/108, 198, 194, 195
See application file for complete search history.

(56) References Cited

U.S. PATENT DOCUMENTS

| | | | |
|---|---|---|---|
| 4,526,175 A | 7/1985 | Chin et al. | 128/344 |
| 4,530,698 A | 7/1985 | Goldstein et al. | 604/271 |
| 4,582,181 A | 4/1986 | Samson | 128/348 |
| 4,604,094 A | 8/1986 | Shook | 604/271 |
| 4,606,347 A | 8/1986 | Fogarty et al. | 128/344 |
| 4,608,984 A | 9/1986 | Fogarty | |
| 4,723,936 A | 2/1988 | Buchbinder et al. | |
| 4,730,616 A | 3/1988 | Frisbie et al. | |
| 4,732,152 A | 3/1988 | Wallsten et al. | 128/343 |

(Continued)

FOREIGN PATENT DOCUMENTS

CA 2 335 130 12/1999

(Continued)

*Primary Examiner*—Vy Q Bui
(74) *Attorney, Agent, or Firm*—Eric J. Sheets

(57) ABSTRACT

The present invention is directed to a deployment system for an endoluminal device. The deployment system includes a confining sheath placed around a compacted endoluminal device. A deployment line is provided in the system that is an integral extension of the sheath. As the deployment line is actuated, the sheath retracts from around the compacted endoluminal device. As the sheath retracts from around the endoluminal device, material from the sheath may be converted into deployment line. Once the sheath is retracted from around the compacted endoluminal device, the endoluminal device expands in configuration and repairs vascular or cardiac structures of an implant recipient. Any remaining sheath material is removed from the implantation site along with the deployment line. The deployment system also includes an endo-prosthesis mounting member placed between the endoluminal device and an underlying catheter. The endo-prosthesis mounting member serves to cushion and retain the endoluminal device when constrained by the sheath and may assist in expansion of the endoluminal device when unconstrained by the sheath.

39 Claims, 13 Drawing Sheets

U.S. PATENT DOCUMENTS

| | | |
|---|---|---|
| 4,846,174 A | 7/1989 | Willard et al. |
| 4,848,343 A | 7/1989 | Wallsten et al. ............. 128/343 |
| 4,875,480 A | 10/1989 | Imbert ........................ 128/313 |
| 4,892,519 A | 1/1990 | Songer et al. |
| 4,960,411 A | 10/1990 | Buchbinder |
| 5,114,414 A | 5/1992 | Buchbinder |
| 5,125,895 A | 6/1992 | Buchbinder et al. |
| 5,192,290 A | 3/1993 | Hilal |
| 5,201,757 A | 4/1993 | Heyn et al. .................. 606/198 |
| 5,242,441 A | 9/1993 | Avitall |
| 5,409,495 A | 4/1995 | Osborn ....................... 606/108 |
| 5,411,509 A | 5/1995 | Hilal |
| 5,445,646 A | 8/1995 | Euteneuer et al. ........... 606/198 |
| 5,456,694 A | 10/1995 | Marin et al. |
| 5,476,589 A | 12/1995 | Bacino ....................... 210/500 |
| 5,501,694 A | 3/1996 | Ressemann et al. |
| 5,527,292 A | 6/1996 | Adams et al. |
| 5,534,007 A | 7/1996 | St Germain et al. ......... 606/108 |
| 5,540,707 A | 7/1996 | Ressemann et al. |
| 5,571,135 A | 11/1996 | Fraser et al. ................ 606/198 |
| 5,593,418 A | 1/1997 | Mollenauer ................ 606/192 |
| 5,628,783 A | 5/1997 | Quiachon et al. |
| 5,639,274 A | 6/1997 | Fischell et al. ................ 604/96 |
| 5,647,857 A | 7/1997 | Anderson et al. ........... 604/264 |
| 5,662,703 A | 9/1997 | Yurek et al. ..................... 623/1 |
| 5,667,490 A | 9/1997 | Keith et al. |
| 5,690,644 A | 11/1997 | Yurek et al. ................. 606/108 |
| 5,693,083 A | 12/1997 | Baker et al. |
| 5,702,364 A | 12/1997 | Euteneuer et al. ............. 604/96 |
| 5,749,920 A | 5/1998 | Quiachon et al. |
| 5,752,934 A | 5/1998 | Campbell et al. |
| 5,769,885 A | 6/1998 | Quiachon et al. |
| 5,772,669 A | 6/1998 | Vrba |
| 5,782,909 A | 7/1998 | Quiachon et al. |
| 5,795,325 A | 8/1998 | Valley et al. |
| 5,814,405 A | 9/1998 | Branca et al. ................ 428/311 |
| 5,824,044 A | 10/1998 | Quiachon et al. |
| 5,836,868 A | 11/1998 | Ressemann et al. |
| 5,843,051 A | 12/1998 | Adams et al. |
| 5,897,567 A | 4/1999 | Ressemann et al. |
| 5,944,726 A | 8/1999 | Blaeser et al. ............... 606/108 |
| 5,957,973 A | 9/1999 | Quiachon et al. |
| 5,968,013 A | 10/1999 | Smith et al. |
| 5,968,069 A | 10/1999 | Dusbabek et al. ........... 606/194 |
| 5,989,280 A | 11/1999 | Euteneuer et al. ........... 606/198 |
| 6,007,543 A | 12/1999 | Ellis et al. ................... 606/108 |
| 6,039,758 A | 3/2000 | Quiachon et al. |
| 6,059,759 A | 5/2000 | Mottola et al. |
| 6,059,813 A | 5/2000 | Vrba et al. ................... 606/198 |
| 6,077,273 A | 6/2000 | Euteneuer et al. ........... 606/108 |
| 6,159,565 A | 12/2000 | Campbell et al. ........... 428/35.7 |
| 6,210,434 B1 | 4/2001 | Quiachon et al. |
| 6,224,627 B1 | 5/2001 | Armstrong et al. |
| 6,235,050 B1 | 5/2001 | Quiachon et al. |
| 6,251,093 B1 | 6/2001 | Valley et al. |
| 6,287,330 B1 | 9/2001 | Johansson et al. |
| 6,322,587 B1 | 11/2001 | Quiachon et al. |
| 6,325,814 B1 | 12/2001 | Euteneuer et al. ........... 606/198 |
| 6,346,118 B1 | 2/2002 | Baker et al. |
| 6,352,561 B1 | 3/2002 | Leopold et al. .............. 623/123 |
| 6,355,061 B1 | 3/2002 | Quiachon et al. |
| 6,371,962 B1 | 4/2002 | Ellis et al. ................... 606/108 |
| 6,375,676 B1 | 4/2002 | Cox |
| 6,391,032 B2 | 5/2002 | Blaeser et al. ............... 606/108 |
| 6,447,521 B1 | 9/2002 | Mouw et al. ................. 606/108 |
| 6,447,540 B1 * | 9/2002 | Fontaine et al. ............. 623/1.12 |
| 6,530,947 B1 | 3/2003 | Euteneuer et al. ........... 623/1.11 |
| 6,533,806 B1 | 3/2003 | Sullivan et al. .............. 623/1.11 |
| 6,540,778 B1 | 4/2003 | Quiachon et al. |
| 6,562,063 B1 | 5/2003 | Euteneuer et al. .......... 623/1.12 |
| 6,592,592 B1 | 7/2003 | Cox ........................... 606/108 |
| 6,610,069 B2 | 8/2003 | Euteneuer et al. ........... 606/108 |
| 6,663,660 B2 | 12/2003 | Dusbabek et al. ........... 623/1.11 |
| 6,663,666 B1 | 12/2003 | Quiachon et al. |
| 6,682,557 B1 | 1/2004 | Quiachon et al. |
| 6,695,862 B2 | 2/2004 | Cox et al. |
| 6,709,454 B1 | 3/2004 | Cox et al. |
| 6,712,827 B2 | 3/2004 | Ellis et al. ................... 606/108 |
| 6,755,854 B2 | 6/2004 | Gillick et al. |
| 6,767,361 B2 | 7/2004 | Quiachon et al. |
| 6,802,849 B2 | 10/2004 | Blaeser et al. ............... 606/191 |
| 6,860,898 B2 | 3/2005 | Stack et al. |
| 6,893,458 B2 | 5/2005 | Cox et al. |
| 6,942,682 B2 | 9/2005 | Vrba et al. |
| 2001/0051822 A1 | 12/2001 | Stack et al. |
| 2002/0052642 A1 | 5/2002 | Cox et al. |
| 2002/0099431 A1 | 7/2002 | Armstrong et al. |
| 2002/0099435 A1 | 7/2002 | Stinson |
| 2003/0028236 A1 | 2/2003 | Gillick et al. |
| 2003/0158597 A1 | 8/2003 | Quiachon et al. |
| 2003/0212451 A1 | 11/2003 | Cox et al. |
| 2004/0122503 A1 | 6/2004 | Campbell et al. |
| 2004/0143272 A1 | 7/2004 | Cully et al. |
| 2004/0143315 A1 | 7/2004 | Bruun et al. |
| 2004/0153143 A1 | 8/2004 | Quiachon et al. |
| 2004/0158315 A1 | 8/2004 | Cox et al. |
| 2005/0015141 A1 | 1/2005 | Quiachon et al. |
| 2005/0033402 A1 | 2/2005 | Cully et al. |

FOREIGN PATENT DOCUMENTS

| | | |
|---|---|---|
| CA | 2 329 213 | 7/2000 |

* cited by examiner

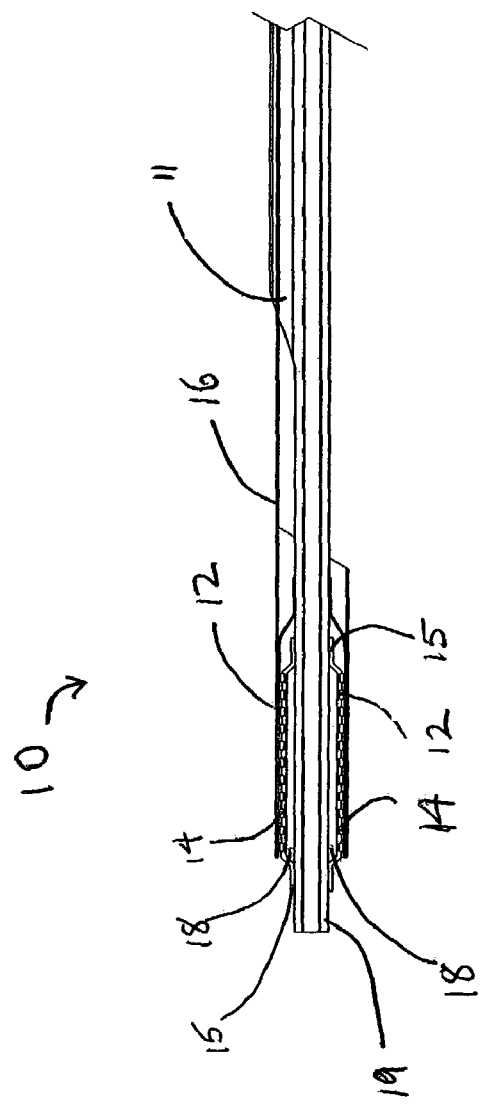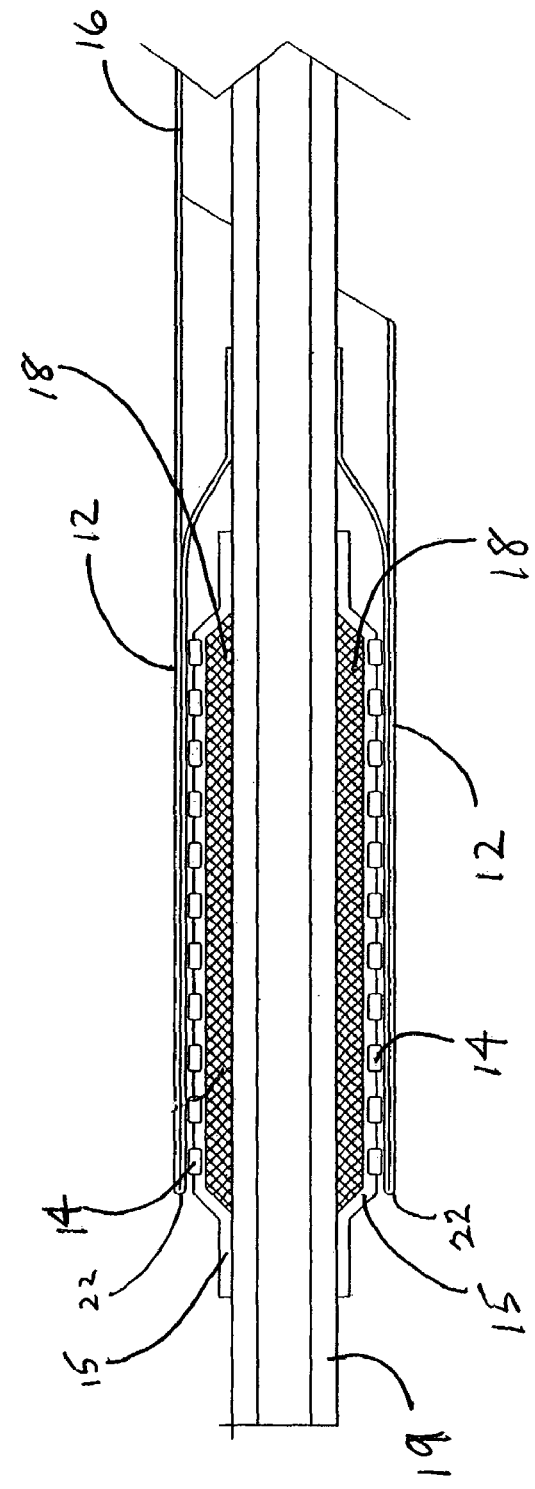

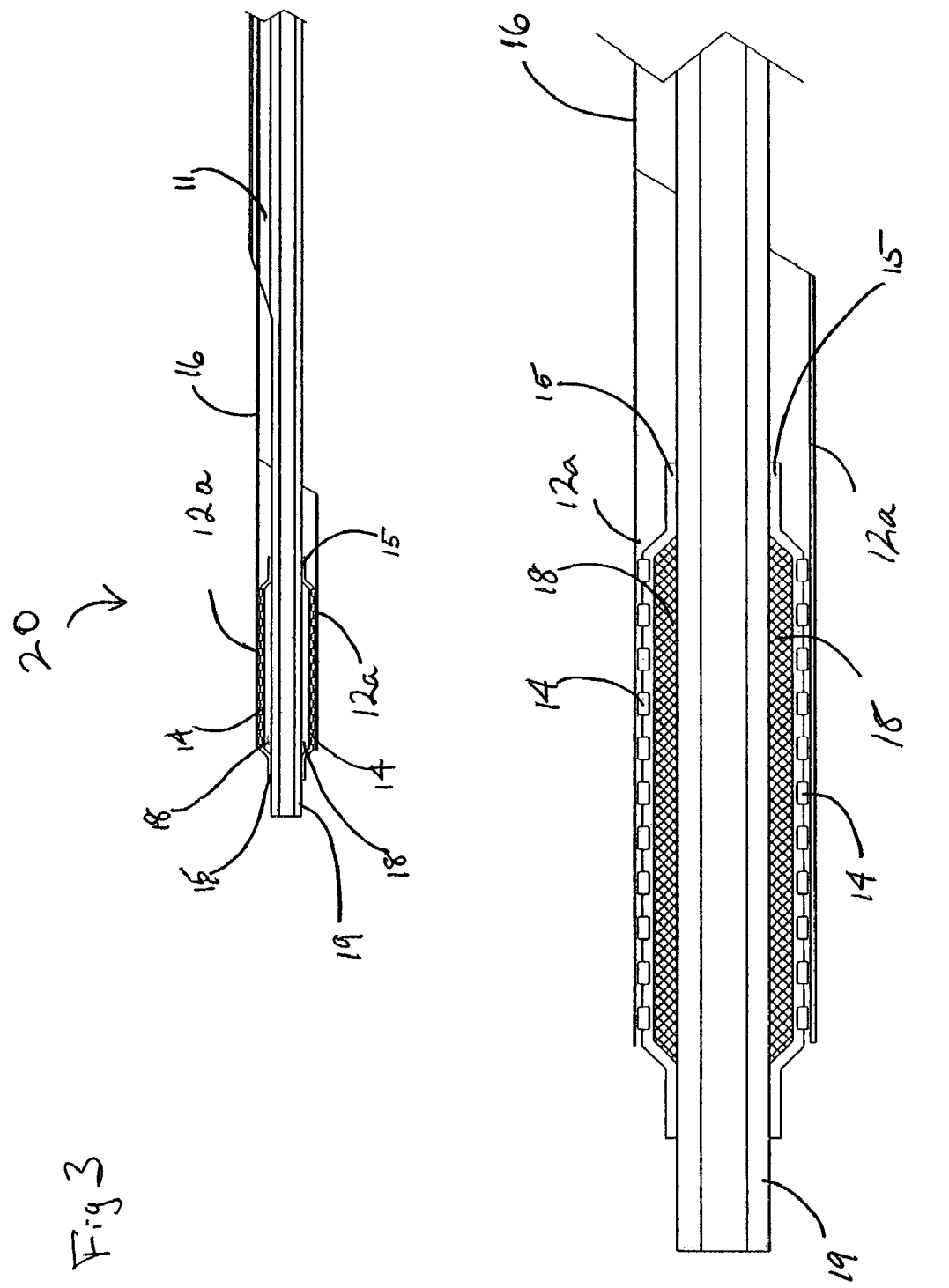

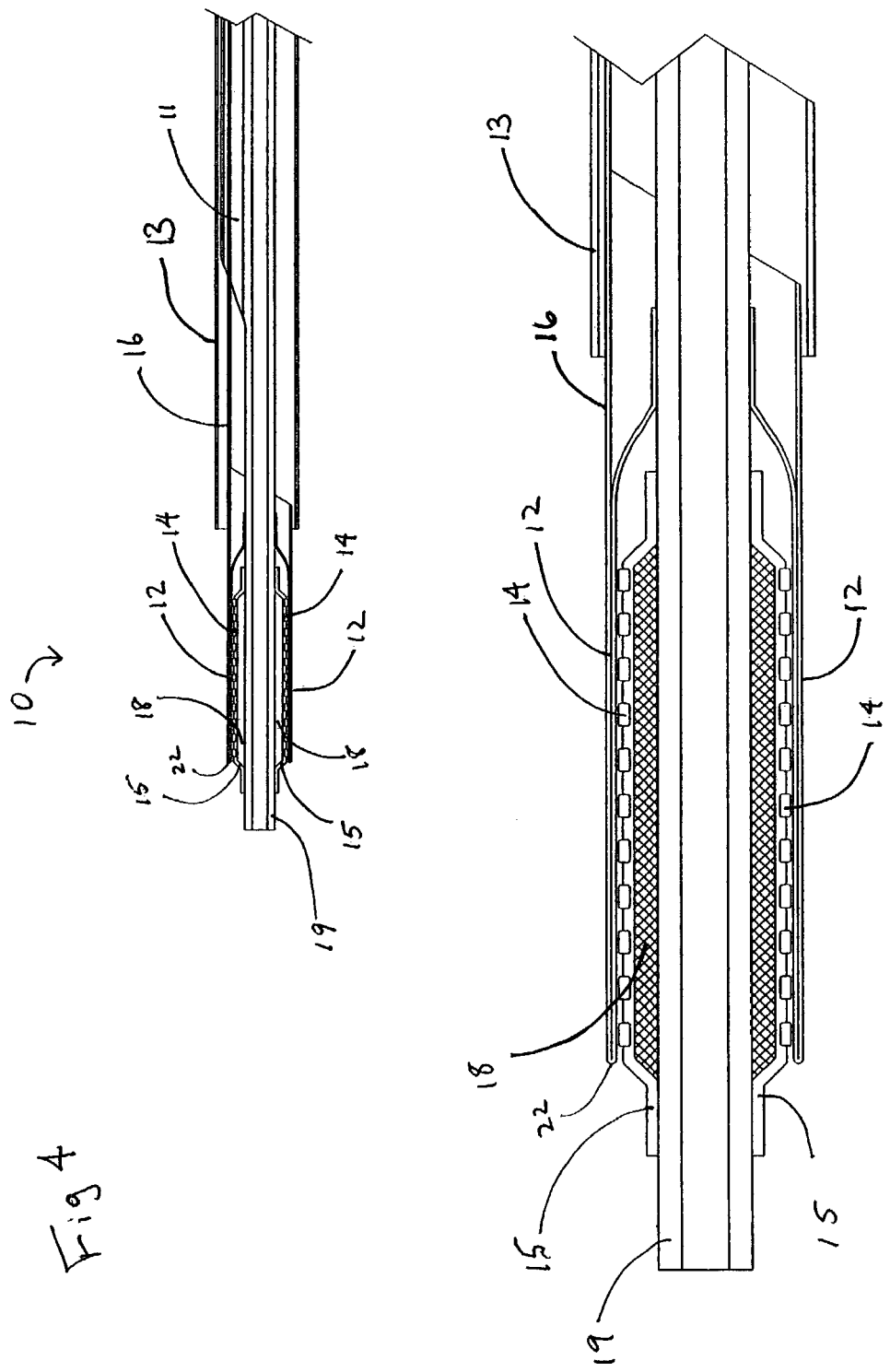

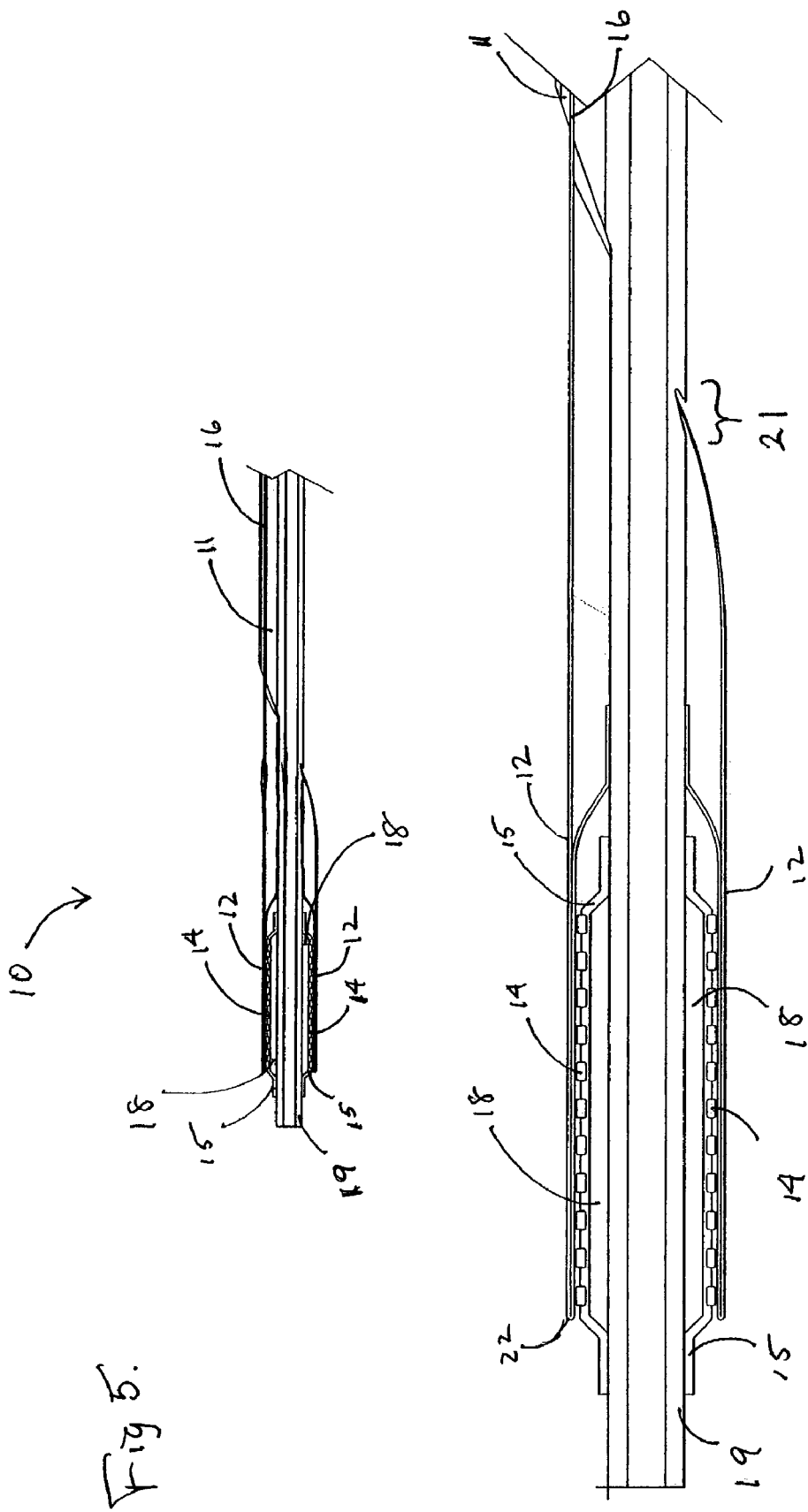

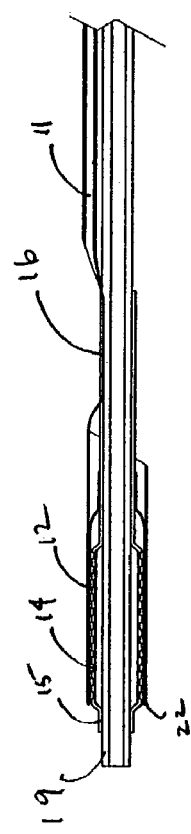

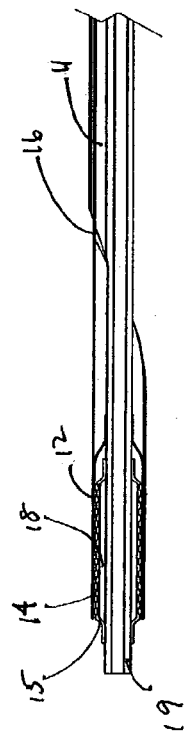
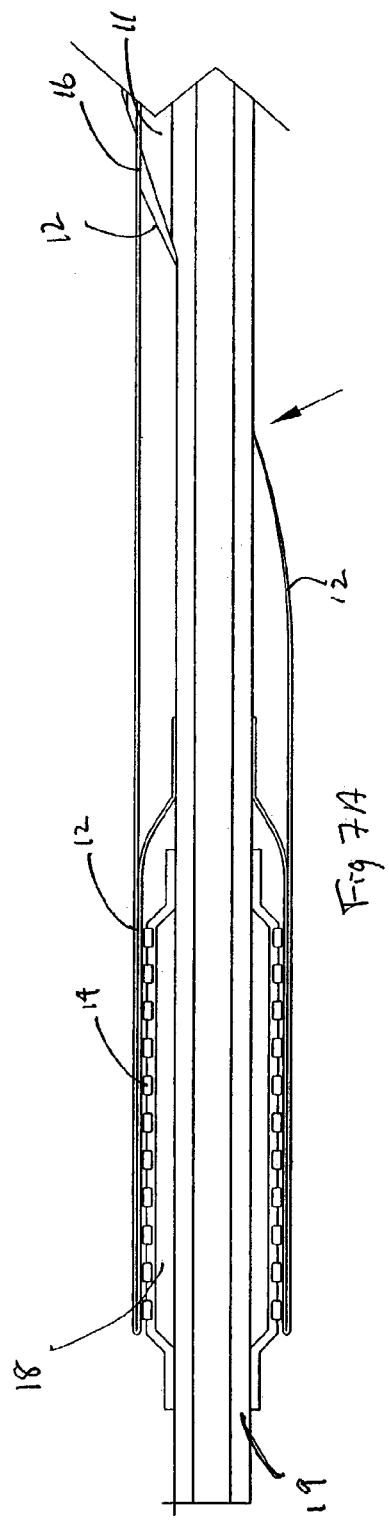
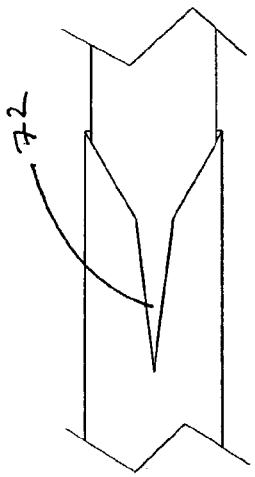
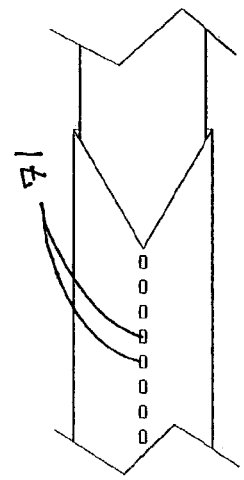

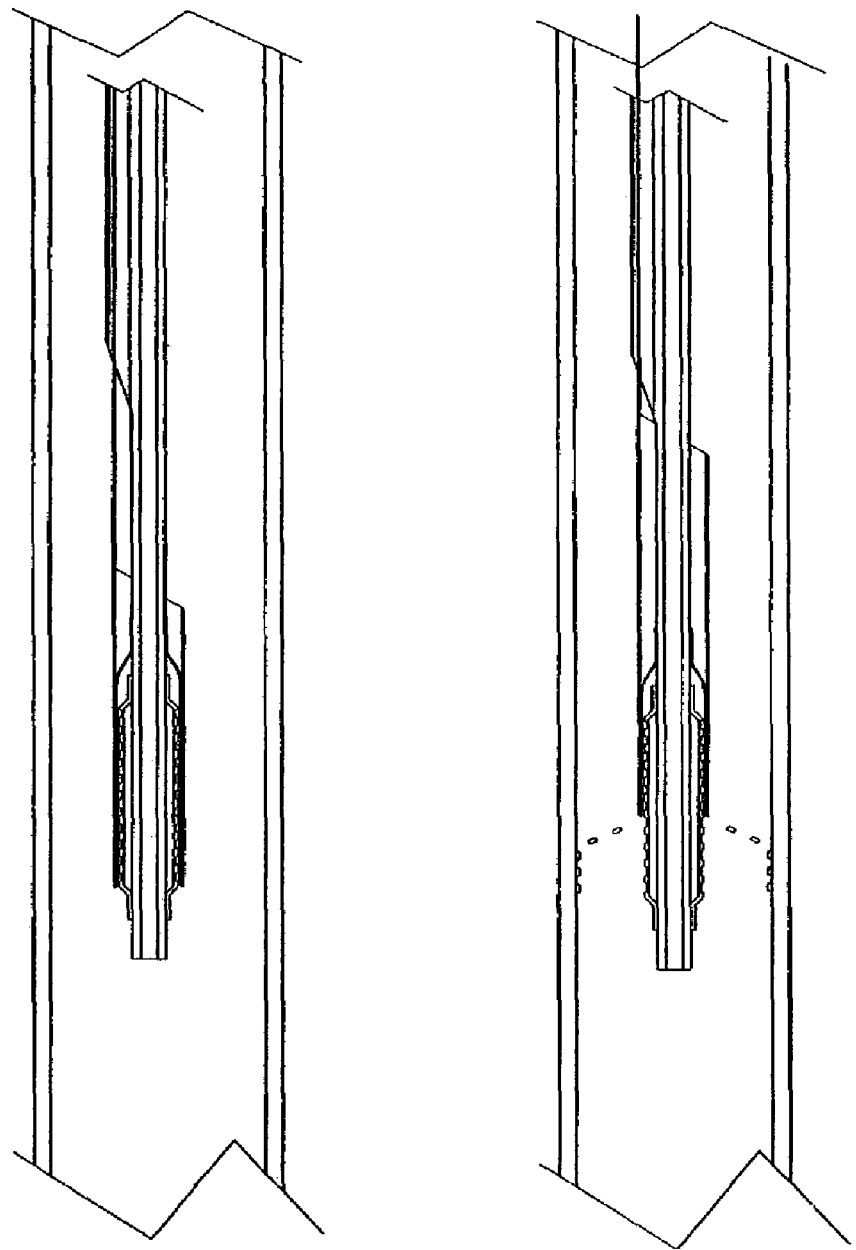

DEPLOYMENT SYSTEM FOR AN ENDOLUMINAL DEVICE

CROSS REFERENCE TO RELATED APPLICATIONS

This application is a continuation-in-part of application Ser. No. 10/346,598 filed Jan. 17, 2003, now U.S. Pat. No. 7,198,636.

FIELD OF THE INVENTION

The present invention relates generally to implantable medical device assemblies. In particular, the invention relates to means for deploying an endoluminal device within vascular or cardiac structures of an implant recipient.

BACKGROUND OF THE INVENTION

Various implantable medical devices for repairing or reinforcing cardiac and vascular structures have been developed in recent years. Some of these devices can be implanted inside a particular vascular or cardiac structure through so-called interventional, or endovascular, techniques. Interventional techniques involve surgically accessing the vascular system through a conveniently located artery or vein and introducing distal portions of a medical device assembly into the vascular system through the arterial or venous access point. Once the medical device assembly is introduced into the vascular system, it is threaded through the vasculature to an implantation site while proximal portions of the assembly having manually operated control means remain outside the body of the implant recipient. The medical device component of the assembly is then deposited at the implantation site and the remainder of the distal portion of the medical device assembly removed from the vascular system through the access point.

Exemplary interventional medical device assemblies include a catheter. The catheter can be used to precisely position the medical device at an implantation site as well as participate in deployment of the medical device at the implantation site. Some catheters have guidewires running their length to aid in positioning and deployment of the medical device. As an alternative to the guidewire, a catheter may be coaxial with an inner sleeve running inside the length of the catheter. The inner sleeve is used to hold an implantable medical device in position while the outer catheter is pulled, causing deployment of the device. Handles, knobs, or other manually operated control means are attached to the opposite end of the catheter in this assembly.

Some implantable medical devices, such as stents, stent-grafts, or other endoluminal devices often require reconfiguration from an initial compacted form to an expanded cylindrical configuration as the device is deployed at an implantation site. These devices can expand on their own by virtue of the design and composition of their structural elements or through the use of an inflatable balloon placed inside the devices.

Self-expanding endoluminal medical devices are maintained in a compacted configuration in a variety of ways. Some devices are maintained in a compacted configuration by simply confining the compacted devices inside a catheter, or similar tool. Other devices are placed inside a sheath following compaction. In these assemblies, a control line is often used to assist in releasing the endoluminal device from the sheath.

In U.S. Pat. No. 6,352,561, issued to Leopold et al., a sheath is formed around an expandable endoluminal device and a control line used to maintain the sheath around the endoluminal device. The sheath is formed by folding a length of polymeric material in half and stitching the opposing edges together with the control line. The stitching pattern permits the control line to be removed from the sheath by pulling on a proximal end of the control line. As the control line becomes unstitched from the sheath, the endoluminal device is progressively released from confinement within the sheath. The control line is removed from the assembly as a distinct entity while the sheath remains at the implantation site.

In U.S. Pat. No. 5,647,857, issued to Anderson et al., an endoluminal device is held in a collapsed configuration over a catheter by a sheath. The assembly is provided with a control line having a free end and an end attached to a collar component of the catheter. The sheath is removed from the endoluminal device by pulling on the control line. As the control line is pulled, it cuts through and splits the sheath material from distal end to proximal end. As the sheath splits open, the endoluminal device is freed to expand. Unlike Leopold et al., the control line remains mechanically attached to the sheath and catheter assembly following deployment of the endoluminal device.

In U.S. Pat. No. 6,447,540, issued to Fontaine et al., a confining sheath is removed from around an endoluminal device with a control line that cuts through and splits the sheath material when pulled by a practitioner, much like Anderson et al. As with Leopold et al, the control line can be completely removed from the assembly as a distinct entity.

In U.S. Pat. No. 5,534,007, issued to St. Germain et al., a single-walled sheath that can collapse and shorten along its, length is placed around a stent. As the distal portion of the sheath is retracted, it uncovers the stent. The uncovered stent is free to expand. A control line can be used to exert a pulling force on the collapsible sheath as a means of removing the sheath from the stent. The control line remains attached to the sheath during and subsequent to deployment of the stent.

In U.S. Pat. No. 6,059,813, issued to Vrba et al, a double-walled confinement sheath for an endoluminal device is described. In an assembly made of these components, the endoluminal device is placed over a catheter shaft in a collapsed configuration. An outer tube is placed in slidable relationship over the catheter. The distal end of the outer tube does not extend to cover the endoluminal device. Rather, the double walled sheath is placed over the collapsed endoluminal device. The inner wall of the sheath is attached to the catheter shaft near the proximal end of the endoluminal device. The outer wall of the double-walled sheath is mechanically attached to the outer tube. Movement of the outer tube relative to the catheter causes the outer wall of the sheath to move past the inner wall of the sheath. Movement of the outer tube in the proximal direction causes the sheath to retract and uncover the underlying endoluminal device. As the sheath retracts, the endoluminal device becomes free to expand. A control line is mechanically attached to the outer tube and serves to move the outer tube and retract the sheath.

None of these medical device assemblies utilize a control line that is integral with a confining sheath. Nor do these assemblies feature a sheath that is convertible to a control line as the sheath is removed from around the endoluminal device. Such an integral control line and confining sheath would preferably be made of a continuous thin-walled material or composite thereof. The thin-walled material would be flexible and exert minimal restrictions on the flexibility of an underlying endoluminal device. Thin-walled materials would also reduce the profile of the sheath and endoluminal device combination. An integral control line and confining sheath would simplify manufacture of control line-sheath constructs by eliminating the need to mechanically attach the control line to the sheath. An integral control line and confining sheath would also eliminate concerns regarding the reliability of the mechanical attachment of the control line to the sheath. Additionally, inclusion of materials, composites, constructions, and/or assemblies exhibiting compliance, compressibility, resilience, and/or expandability when positioned between the sheath-constrained endoluminal device and the delivery catheter would serve to cushion and retain the endoluminal device beneath the confining sheath on a delivery catheter, as well as assist in expansion of the endoluminal device in some embodiments.

SUMMARY OF THE INVENTION

The present invention is directed to a deployment system for an endoluminal or endo-prosthetic device. In preferred embodiments, the endoluminal device is self-expanding as a consequence of the device design and the materials used to construct the device. In other embodiments, the endoluminal device is expandable with an inflatable balloon or other dilation means placed within the device. In yet other embodiments, the endoluminal device is an inflatable balloon. The endoluminal device is maintained in a compacted, or collapsed, configuration by a removable sheath. In preferred embodiments, the removable sheath is removed from around the endoluminal device by applying tension to a deployment line. The deployment line is an integral, continuous, extension of the sheath and is made of the same material as the sheath. As the deployment line is pulled, the sheath is progressively removed from around the endoluminal device and also functions as an extension of the deployment line. When the sheath has been substantially removed from around a portion of the endoluminal device, that portion of the endoluminal device is free to expand. Removal of the sheath may be continued until the entire endoluminal device is freed from radial constraint. The deployment line, along with any remaining sheath material, may be removed from the implantation site through a catheter used to deliver the sheathed endoluminal device to the site.

In embodiments employing an endoluminal device in the form of a stent, the sheath may be removed from around the stent by inflating a balloon or other dilation means located within the collapsed lumen of the stent and expanding the stent against the sheath until the sheath is removed through the action of an indwelling balloon or other dilation means. The sheath is removed with the aid of the deployment line portion of the present invention and/or a mechanism capable of storing and releasing kinetic energy. A seen in FIG. 13, the mechanism is referred to herein as an "active elastic element (25)" and is preferably in the form of spring elements incorporated into the deployment line portion and/or the sheath portion of the present invention. Alternatively, active elastic elements can be in the form of rubber bands and elastomeric polymers, including fluoroelastomers.

The removable sheath is made of one or more thin, flexible polymeric materials including composites thereof. The sheath ordinarily assumes the form of a continuous thin-walled tube when constraining an endoluminal device. Such a thin-walled sheath exerts minimal resistance to longitudinal flexing of the underlying endoluminal device. The thin-walled sheath also reduces the profile of the sheath-endoluminal device combination, when compared to conventional constraints. In preferred embodiments, a double-walled tubular sheath is used. Double walls enable the sheath to be retracted from around an endoluminal device by sliding one wall past the other wall. As the sheath is retracted, or unrolled, in this manner, the sheath portion does not rub or scrape against the underlying endoluminal device. This is particularly advantageous when coatings containing medications, and/or pharmaceuticals are placed on surfaces of the endoluminal device that could be disrupted by a sheath that rubs or scrapes against the endoluminal device as the sheath is removed from the device.

The deployment line is formed from the same material as the removable sheath and is an integral extension of the sheath material. In some embodiments, the deployment line portion (16) extends from the sheath portion (12, 12a) through a delivery catheter to a control knob (not shown) located at the proximal end of the catheter (FIGS. 3-7). Among these embodiments, the sheath portion extends proximally beyond the endoluminal device toward the distal end of the deployment system (FIG. 5). In preferred embodiments, the sheath extends over the underlying delivery catheter a desired length to a point at which the sheath portion transforms to the deployment line portion (FIG. 7). In more preferred embodiments, the sheath portion extends substantially the entire length of the delivery catheter before transforming into deployment line. In the most preferred embodiment (FIG. 11), at least a portion of the sheath-deployment line construction (12) is enclosed within a secondary catheter (19a), catheter lumen, or other containment device such as an expanded porous polytetrafluoroethylene tube. Pulling on the control knob actuates the deployment line. Once the deployment line is actuated, the removable sheath begins to move, or retract, from around the endoluminal device.

In one embodiment, as removed sheath material travels beyond the receding end of the sheath, the sheath begins to become converted to deployment line. Conversion of the sheath into the deployment line usually begins at a point where the tubular sheath breaks apart, separates, and converges into deployment line material. In preferred embodiments, means are provided for initiating or sustaining the conversion of the sheath to deployment line. These means may take the form of perforations, stress risers, or other mechanical weaknesses introduced into the sheath material. The means can also be cutting edges or sharp surfaces on the delivery catheter.

In preferred embodiments, materials, composites, constructions, and/or assemblies exhibiting compliance, compressibility, resilience, and/or expandability are placed between the endo-prosthesis, or endoluminal device, and the delivery catheter to provide an "endo-prosthesis mounting member." An endo-prosthesis mounting member serves to cushion the endoluminal device when constrained by the sheath and may assist in expansion of the device when unconstrained. An endo-prosthesis mounting member also serves to anchor and retain the endoluminal device in place around an underlying catheter shaft, while minimizing the profile of the deployment system. Anchoring the endoluminal device with an endo-prosthesis mounting member eliminates the need for barrier, or retention, means at either end of the endoluminal device. The absence of barrier means contributes to a reduction in the profile of the deployment system as well as increasing the flexibility of the distal portion of the system. The present invention can also be provided with an additional catheter or catheter lumen for the sheath-deployment line in order to prevent the deployment line portion from leaving the general path established by the delivery catheter. In one embodiment, the endo-prosthesis mounting member is in the form of an inflatable, or otherwise expandable, balloon. The present invention can be used alone or in combination with other endo-prosthesis delivery means. Multiple endo-prosthetic devices can also be delivered with the present invention.

Accordingly, one embodiment of the present invention is a deployment system for an endoluminal device comprising an expandable endoluminal device mounted on a delivery catheter provided with an endo-prosthesis mounting member, a removable sheath adapted to cover the endoluminal device, the sheath comprising a fluoropolymer material adapted to surround at least a portion of the endoluminal device and constrain the device in an introductory profile, wherein the deployment system includes a deployment line integral with the sheath to effectuate device deployment, and wherein upon deployment, the sheath separates from the endoluminal device through actuation of the deployment line, the sheath becoming removed from the device along with the deployment line.

In another embodiment, the present invention is a deployment system for an endoluminal device comprising an expandable endoluminal device placed over an endo-prosthesis mounting member and at least partially enclosed by a removable sheath, and a deployment line integral with the removable sheath, wherein the removable sheath is convertible to the deployment line as the sheath is removed from the endoluminal device.

These enhanced features and other attributes of the deployment system of the present invention are better understood through review of the following specification.

BRIEF DESCRIPTION OF THE DRAWINGS

FIG. 1 illustrates a longitudinal cross-section of the present invention.

FIG. 1A is an enlarged view of FIG. 1.

FIG. 3 illustrates a longitudinal cross-section of the present invention.

FIG. 3A is an enlarged view of FIG. 3.

FIG. 4 illustrates a longitudinal cross-section of the present invention.

FIG. 4A is an enlarged view of FIG. 4.

FIG. 5 illustrates a longitudinal cross-section of the present invention.

FIG. 5A is an enlarged view of FIG. 5.

FIG. 6 illustrates a longitudinal cross-section of the present invention.

FIG. 6A is an enlarged view of FIG. 6.

FIG. 7 illustrates a longitudinal cross-section of the present invention.

FIG. 7A is an enlarged view of FIG. 7.

FIG. 7B illustrates the embodiment of FIG. 7A as viewed from the direction indicated by the arrow.

FIG. 7C illustrates the embodiment of FIG. 7A as viewed from the direction indicated by the arrow.

FIGS. 8 and 8A illustrate longitudinal cross-sections views of the present invention placed inside a vascular or cardiac structure.

DETAILED DESCRIPTION OF THE INVENTION

Figure 12:
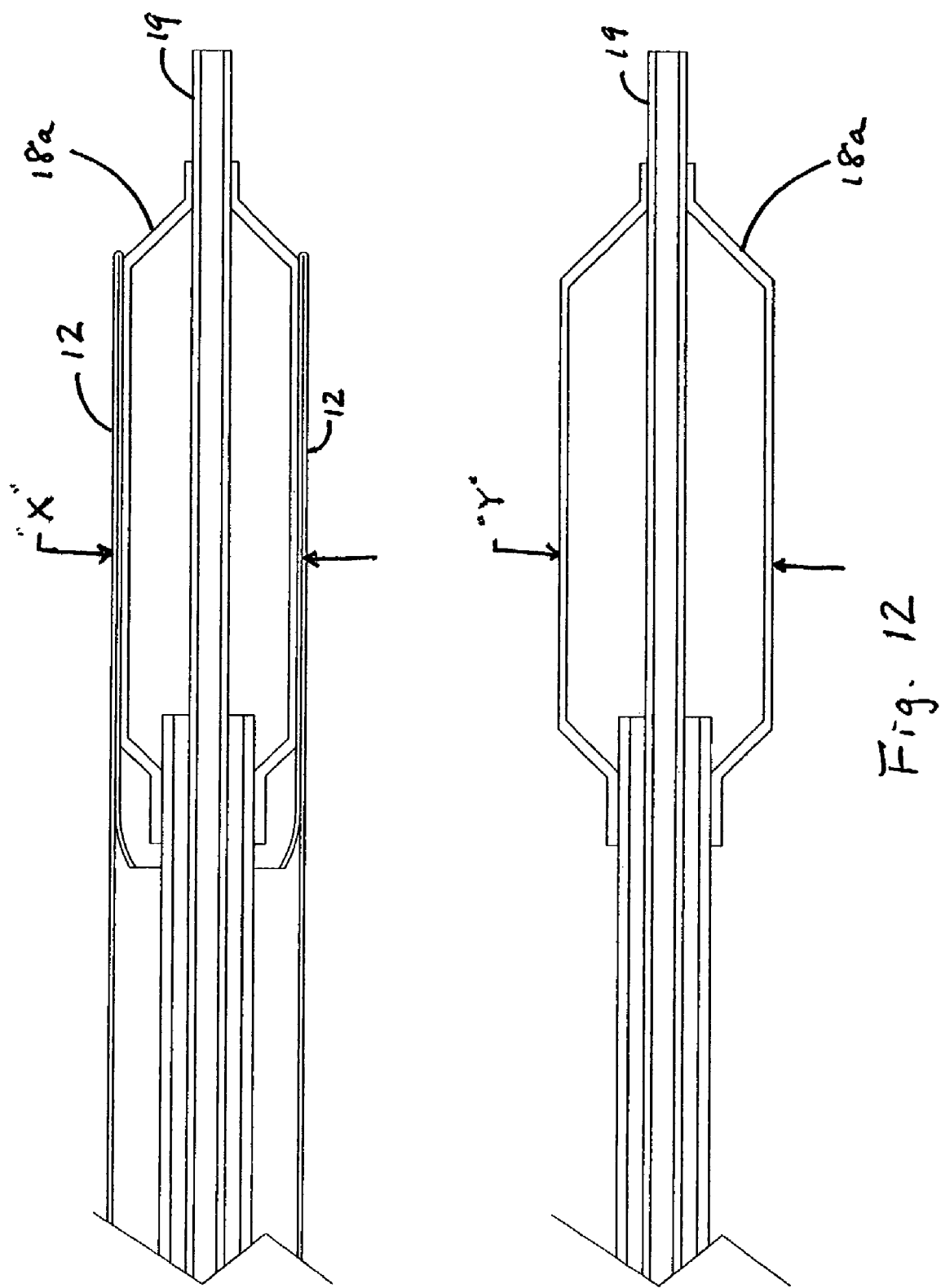
FIG. 12 illustrates a longitudinal cross-section of the present invention showing an endoluminal device in the form of a collapsed inflatable balloon having a first dimension confined to a second dimension with a sheath-deployment line of the invention.
Figure 13:
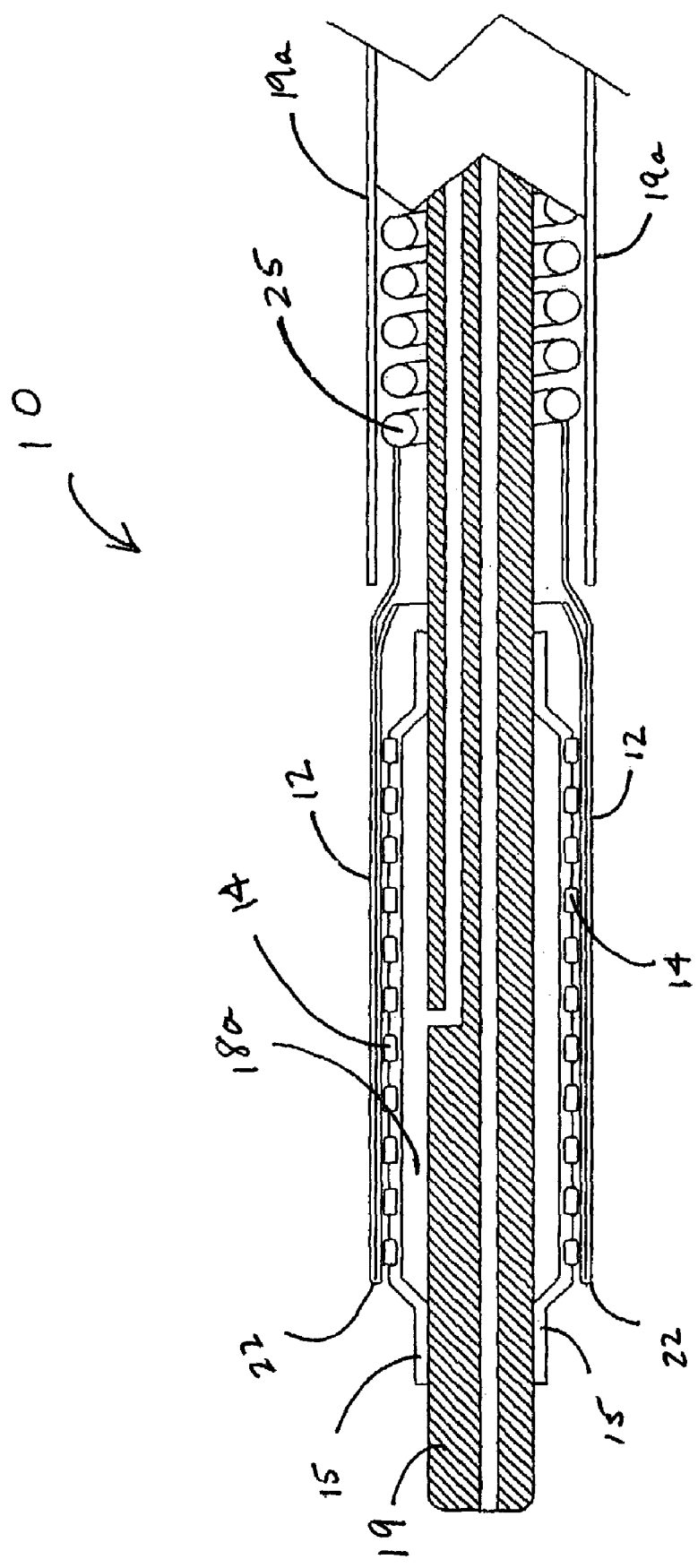
FIG. 13 illustrates a cross-section of the present invention showing an active elastic element attached to the sheath portion of the present invention as a means to remove the sheath from around an endoluminal device.

The present invention is directed to a deployment system for an endoluminal device having a removable sheath with a deployment line or filament that is an integral part of the sheath. As indicated by the relative difference in the space between the "x" arrows and the "y" arrows in FIG. 12, the sheath portion (12) confines the endoluminal device (18a) to a smaller profile than is possible without the sheath. The sheath radially confines the endoluminal device in a compacted or collapsed configuration during storage and introduction into a patient's vascular system. The confining sheath maintains the endoluminal device in a compacted configuration until the device is delivered with a catheter to an implantation site in a vascular or cardiac structure. At the time of deployment, the sheath is retracted from the endoluminal device. In some embodiments, sheath material may be converted into deployment line material as the sheath is removed from the endoluminal device. As the sheath is removed from the endoluminal device, the endoluminal device is free to expand. Once free from the confining sheath, the endoluminal device may expand spontaneously or with the assistance of an inflatable balloon. Any remaining sheath material may be removed from the implantation site along with the deployment line.

The integral sheath-deployment line is preferably a flexible polymeric material that is continuous along the length of the construct. Preferably, the physical and mechanical properties of the sheath portion are such that they are uniform and homogeneous throughout the length of the sheath portion used to constrain the endoluminal device. Since most endoluminal devices are generally circularly cylindrical in form, the sheath is preferably tubular in shape in order to enclose most or all of the endoluminal device. Conical, tapered, or other suitable shapes for the sheath are also contemplated in the present invention. Flexibility of the sheath is enhanced by making the walls of the sheath as thin as practicable. In one embodiment of the present invention (20), the tubular sheath portion (12a) of the sheath-deployment line has a single wall (FIG. 3). The deployment line portion can extend from either end of the single-walled sheath (12a). When the sheath portion is retracted from around an endoluminal device, the length of retracted sheath is substantially equal to the length of deployment line displaced during deployment of the endoluminal device.

In another embodiment of the present invention (10), the sheath portion (12) of the sheath-deployment line has a double wall (FIGS. 1, 2, and 4-11). In a preferred embodiment, the double walled-sheath portion (12) is made of a polymeric material that is folded on itself. The double-walled sheath portion is placed over the endoluminal device (14) so that the fold (22) is positioned at the distal end (i.e., farthest from the control knob) of the sheath portion (12). The inner wall of the sheath portion may be anchored to part of an underlying delivery catheter (19) proximal to the endoluminal device (14). In preferred embodiments, the sheath portion (12) is not attached to the delivery catheter (19). The proximal end of the outer wall of the sheath has at least one portion, or integral extension, that is convertible to deployment line (16). Space between the walls of the double-walled sheath portion can be filled with fluids, lubricants, pharmaceutical compositions, and/or combinations thereof. The deployment line (16) is routed through the delivery catheter (19) to a control knob (not shown) located at the proximal end of the deployment system (10). Alternatively, a separate catheter (13) or catheter lumen (11) is provided for the deployment line (FIGS. 4 and 1, respectively). These embodiments provide additional containment of the deployment line portion, particularly when bends or curves in a patient's vasculature having small radii are anticipated. In the most preferred embodiment (FIG. 11), the sheath portion of the sheath-deployment line construction extends substantially the entire length of the delivery catheter (19) and is confined within a separate catheter (19a) or catheter lumen. The deployment line portion is formed near the proximal end of the deployment system and is attached to a control knob (not shown).

Preferably, the physical and mechanical properties of the sheath portion are such that they are uniform and homogeneous throughout the length of the sheath portion used to constrain the endoluminal device. When the sheath portion is retracted from around an endoluminal device, the length of retracted sheath is essentially half the length of deployment line displaced during deployment of the endoluminal device. This two to one ratio of length of deployment line removed to length of sheath material removed reduces the effect of too rapid or strong a pull on the deployment line on release of the endoluminal device from the sheath.

Fluoropolymer materials are preferred for making the retractable tubular constraining sheath-deployment line constructs of the present invention. Fluoropolymer materials used in the present invention are strong, thin, and lubricious. The lubriciousness of the fluoropolymer materials is especially advantageous in embodiments utilizing a sheath-deployment line having walls that slide past one another or over an endoluminal device. Particularly preferred fluoropolymer materials are porous expanded polytetrafluoroethylene materials alone or in combination with fluorinated ethylene propylene materials. Most preferred fluoropolymer materials are strong and thin, such as those described in Example 2, infra. The sheath-deployment line is made by constructing an appropriate tube from layers of film and/or membrane. The sheath-deployment line may also be constructed from extrusions of polymeric materials. The extrusions can be used alone or in combination with film/membrane materials. Once constructed, a significant portion of the tube is rendered filamentous by rolling and heating.

The sheath may be converted to deployment line by pulling on the deployment line and causing the sheath material to separate and converge into a single filament. As sheath material is converted to deployment line by this process, the edge of the sheath supplying material to the deployment line recedes causing the sheath to retract from around the endoluminal device. As a portion of the sheath retracts, the portion of the endoluminal device confined by the sheath is freed to expand (FIGS. 8-8A). Means are optionally provided to the deployment system that initiate or sustain the conversion of sheath to deployment line. As shown in FIG. 7, the means include perforations (71), cutouts (72), or other engineered defect introduced into the sheath material. As shown in FIG. 5, the means also include cutters (21) or other sharp edges on the delivery catheter. Such cutting means may be formed on the delivery catheter by exposing a strand of reinforcing stainless steel from within the catheter and adapting the strand to cut into the sheath portion.

Figure 2:
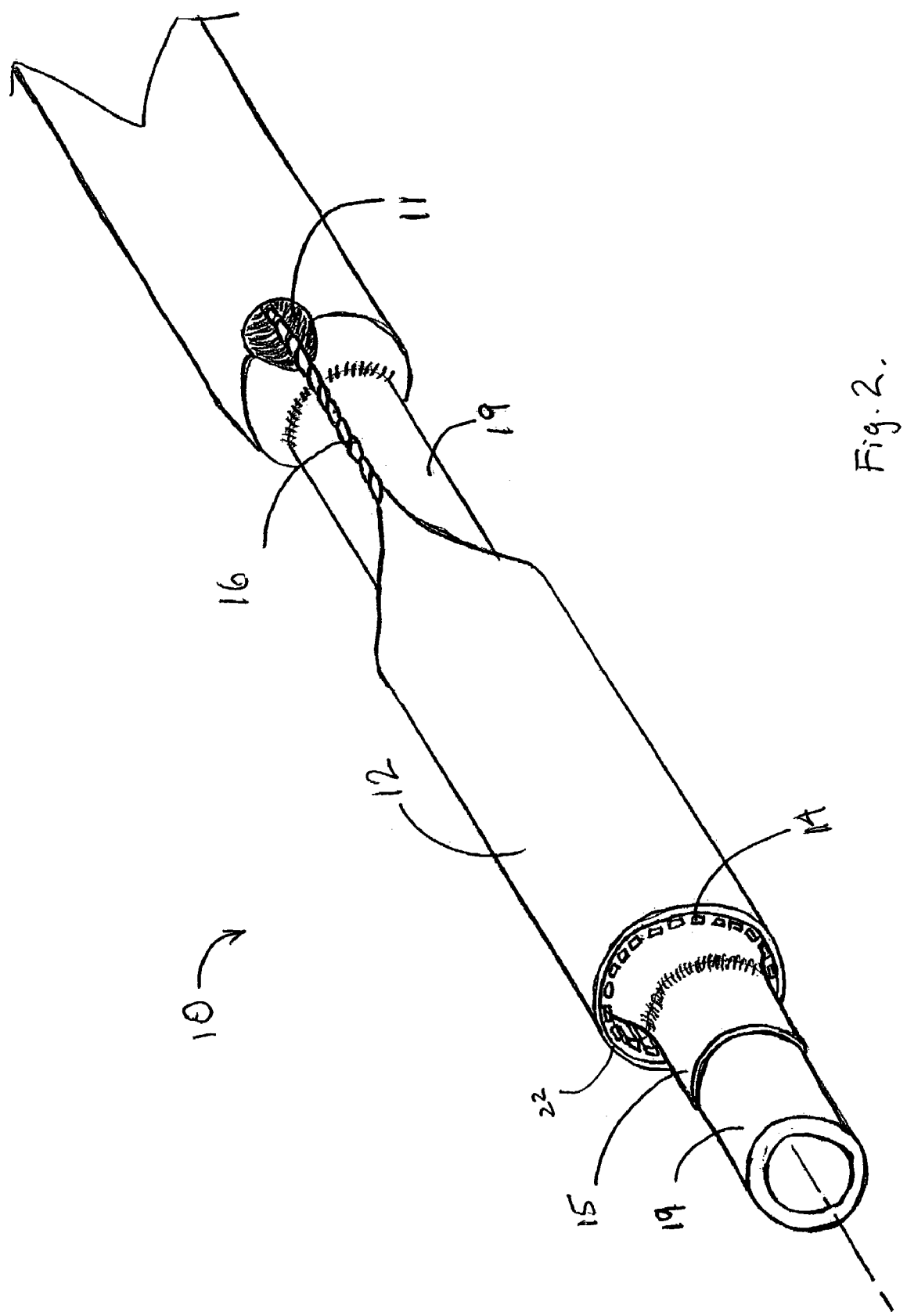
FIG. 2 illustrates a perspective view of the present invention.
Figures 9, 9A:
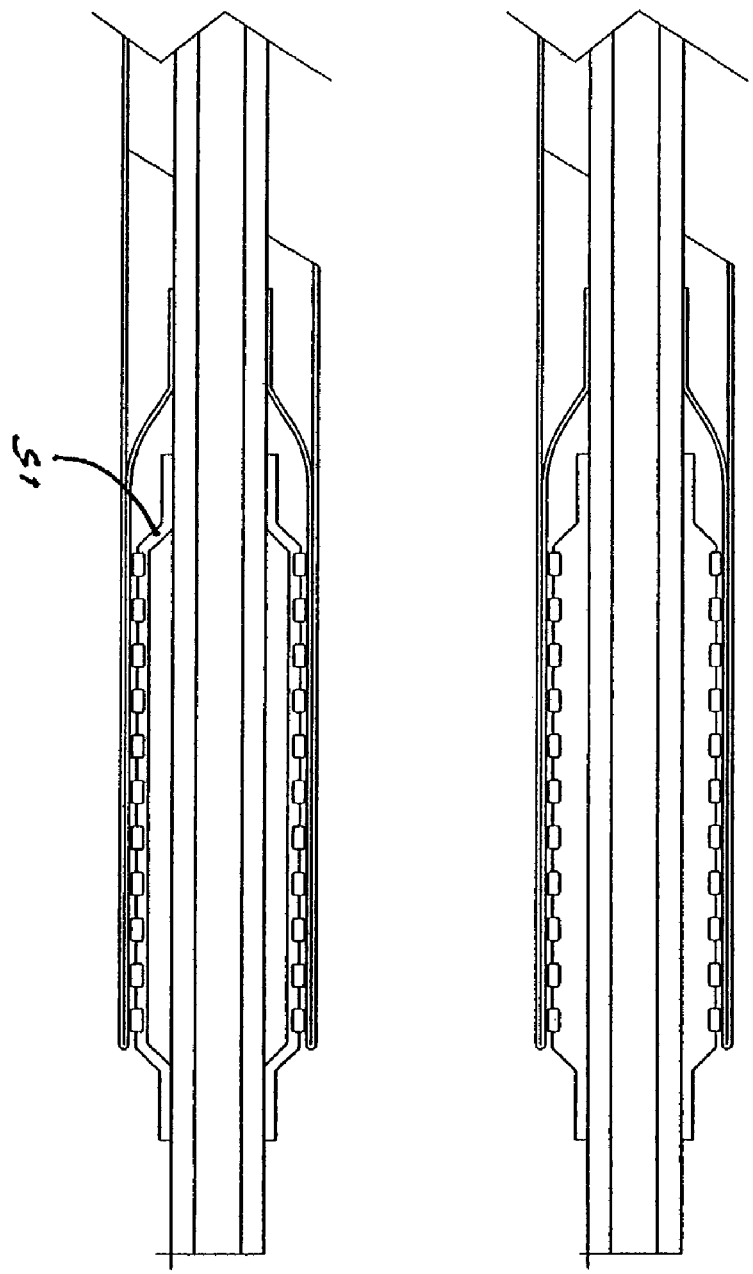
FIG. 9 illustrates a longitudinal cross-section of the present invention with a covering placed over an endo-prosthesis mounting member.
FIG. 9A illustrates a longitudinal cross-section of the present invention without a covering placed over an endo-prosthesis mounting member.
Figure 10:
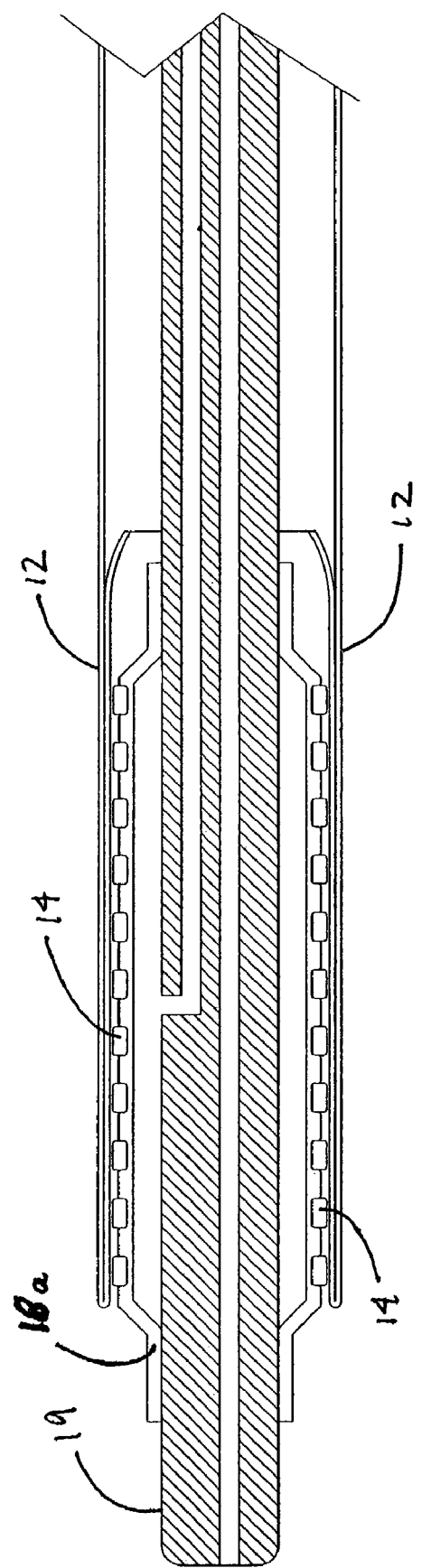
FIG. 10 illustrates a longitudinal cross-section of the present invention with an endo-prosthesis mounting member placed between an underlying delivery catheter and an endoluminal device.
Figure 11:
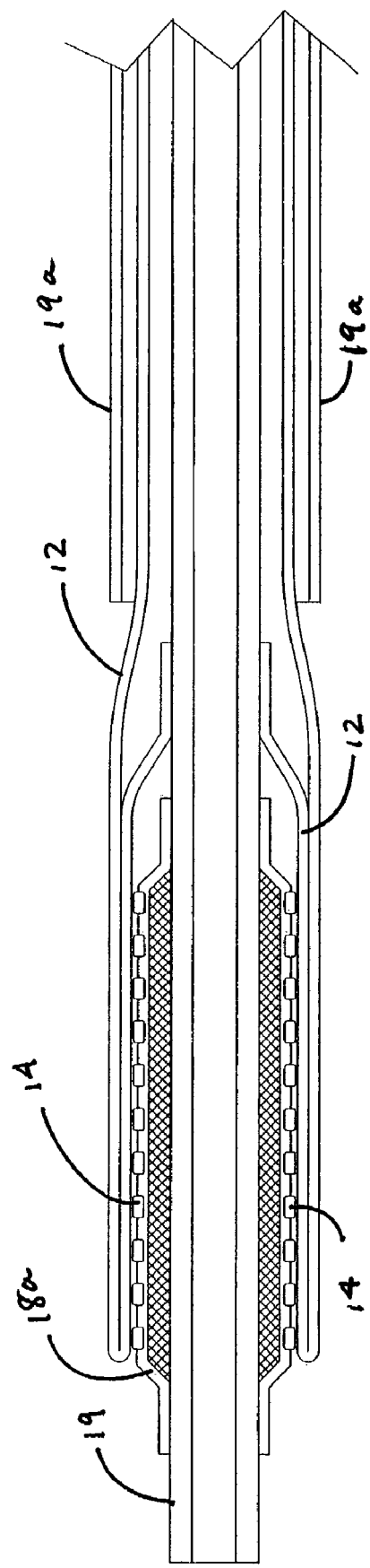
FIG. 11 illustrates a longitudinal cross-section of the present invention having an outer catheter, or tube, placed over substantially the entire length of a sheath-deployment line construction.

In the preferred embodiment of the present invention, materials, composites, constructions, and/or assemblies exhibiting compliance, compressibility, resilience, and/or expandability are placed between the endoluminal device and the delivery catheter to form an "endo-prosthesis mounting member (18)." The endo-prosthesis mounting member can be covered (15) or uncovered (FIG. 9). At least a portion of the endoluminal device is pressed into a covered or uncovered endo-prosthesis mounting member to anchor the endoluminal device on the delivery catheter and prevent the endoluminal device from moving along the length of the catheter. Materials with a tacky surface are useful with the endo-prosthesis mounting member, particularly in combination with a lubricious sheath material. The endo-prosthesis mounting member eliminates the need for barrier, or retention, means placed at the proximal and distal end of the endoluminal device. In addition to added flexibility imparted to the deployment system without the barrier means, the profile of the sheath and endoluminal device combination is reduced without the barrier means. In yet another embodiment, the endo-prosthesis mounting member is in the form of an inflatable balloon (FIG. 10, part 18a). Suitable materials for the endo-prosthesis mounting member include, but are not limited to, silicones, silicone foams, polyurethane, polyurethane foams, and polytetrafluoroethylene foams or combinations thereof. The endo-prosthesis mounting member is attached to the outer wall of the delivery catheter with adhesives, heat, or other suitable means.

A non-inflatable endo-prosthesis mounting member is preferably enclosed with a covering (15) in the form of a polymeric material. The polymeric material is preferably a fluoropolymer-based material. Porous expanded polytetrafluoroethylene is the preferred fluoropolymer for enclosing the compressible material. Other suitable polymeric materials include, but are not limited to, silicone, polyurethane, polyester, and the like.

EXAMPLES

Example 1

This example describes the construction of a deployment system of the present invention. Construction of the system began with the preparation of a distal catheter shaft for receiving an expandable stent. Once the distal catheter was prepared, the expandable stent was placed within a sheath-deployment line. The distal catheter portion of this combination was attached to a primary catheter shaft. The deployment line portion was then routed through the primary catheter to a control knob. The control knob was part of a hub located proximally on the primary catheter. The sheath portion of the sheath-deployment line was in the form of a single-walled tube.

A tubular material three inches long was obtained from Burnham Polymeric, Inc., Glens Falls, N.Y. for use as the distal catheter shaft. The tube was made of a polyether block amide material, commonly known as PEBAX® resin and reinforced with a stainless steel braid. The outer diameter (OD) was 1.01 mm and the inner diameter (ID) was 0.76 mm.

An endo-prosthesis mounting member in the form of a compressible material was then placed on the catheter.

To place the endo-prosthesis mounting member on the catheter, the catheter was mounted on a mandrel having an outer diameter of 0.74 mm. A film of porous expanded polytetrafluoroethylene (ePTFE) was obtained according to the teachings in U.S. Pat. No. 5,814,405, issued to Branca, which is incorporated herein by reference. A discontinuous coating of fluorinated ethylene propylene (FEP) was applied to one side of the ePTFE material in accordance with U.S. Pat. No. 6,159,565, issued to Campbell et al., and incorporated herein by reference. An edge of the ePTFE-FEP composite film two inches wide was attached with heat to the catheter shaft. After initial attachment, the film was wrapped around the catheter shaft forty-five (45) times under light tension. With every fifth wrap of the film, and on the final layer, the film is further attached to itself with heat supplied by a soldering iron.

This procedure provided a endo-prosthesis mounting member in the form of a compressible material, or compliant "pillow," on the distal catheter shaft. The expandable stent was mounted over the endo-prosthesis mounting member. The endo-prosthesis mounting member provides a means of retaining an expandable stent on the catheter shaft during storage, delivery to an implantation site, and deployment of the expandable stent at the implantation site. Optionally, the endo-prosthesis mounting member may be reinforced with a thin coating of an elastomeric material such as silicone, urethane, and/or a fluoroelastomer.

An eight (8) cell, 6 mm diameter, nitinol stent was obtained from Medinol Ltd., Tel-Aviv, Israel. The stent was placed over the endo-prosthesis mounting member of the catheter in an expanded state. The combination was placed within a machine having a mechanical iris that compacts or compresses the stent portion of the assembly onto the endo-prosthesis mounting member. While retained in the mechanical iris machine, the stent was reduced in temperature from room temperature (c. 22° C.) to approximately five degrees centigrade (5° C.). At the reduced temperature, the iris machine was actuated to compact, or collapse, the stent onto the endo-prosthesis mounting member. While in the refrigerated and compressed configuration, the catheter, endo-prosthesis mounting member, and stent were placed within a sheath-deployment line of the present invention.

The sheath-deployment line having a length equal to, or greater than, the length of the final deployment system was made as follows. A length of stainless steel mandrel (c. 1 m) measuring 1.89 mm in diameter was covered with a tubular extruded ePTFE material having an overall length of about 200 cm. The tubular ePTFE material had an outer diameter of 1.41 mm, a wall thickness of 0.05 mm, and an average longitudinal tensile strength of 3.52 kgf with an average circumferential strength of 0.169 kgf. The tubular ePTFE material also had an average mass/length of 0.0473 g/ft with an average Matrix Tensile Strength of 69,125 PSI. At one end (proximal end), the tubular ePTFE material was bunched together on the mandrel, while the opposite end (distal end) of the ePTFE material remained smooth on the mandrel.

The first few centimeters of the tubular ePTFE material was sacrificed and the next 5 cm of the distal end (smoothed end) of the extruded ePTFE material was then reinforced with a composite fluoropolymer material as follows. The ePTFE-covered mandrel was attached to retaining chucks on a film-wrapping machine. A first reference line located approximately 5 cm from the end of the smooth portion of the extruded ePTFE material was circumferentially drawn around the material with a permanent marker (SHARPIE®). A 5 cm wide composite membrane made of expanded polytetrafluoroethylene (ePTFE) and fluorinated ethylene propylene (FEP) was applied proximal from the first reference line on the extruded ePTFE material so the FEP portion of the composite membrane was against the extruded ePTFE material. The composite membrane was wrapped around the ePTFE covered mandrel two times so that the primary strength of the extruded ePTFE material was oriented perpendicular to the longitudinal axis of the mandrel. The composite membrane was initially tacked in place on the extruded ePTFE material with heat applied from a soldering iron. The composite ePTFE/FEP material had a density of about 2.14 g/cm$^3$, a thickness of 0.005 mm, and tensile strengths of about 340 KPa (about 49,000 psi) in a first direction and of about 120 KPa (about 17,000 psi) in a second direction (perpendicular to the first direction). The tensile measurements were performed on an Instron Tensile Machine (Instron Corporation, Canton, Mass.) at 200 mm/min. load rate with 2.5 cm (one inch) jaw spacing.

Material of the sheath-deployment line construction adjacent to the reinforced portion was smoothed out along the mandrel and a second reference line was drawn around the material 5 cm from the first reference line.

A second portion of the sheath-deployment line construction was reinforced as follows. A second reference line was drawn around the extruded ePTFE material 5 cm from the proximal end of the first reinforced portion. Using the second reference line to align a 2 cm wide strip of the above-mentioned ePTFE/FEP composite membrane, the composite membrane was wrapped once around the remaining portion of the extruded ePTFE material to form a second reinforced portion of the sheath-deployment line of the present invention. The second reinforced portion was about 2 cm in length. The composite reinforcing membrane material was attached to the extruded ePTFE material as described above, with the exception that the major strength component of the material was parallel to the axis of the mandrel.

Any air trapped in the construction was removed by applying a sacrificial layer of ePTFE tightly around the construction. A one inch (2.54 cm) wide film of ePTFE was helically overwrapped around the reinforced portion of the construction. Two layers of the ePTFE film were applied in one direction and two layers were applied in the opposite direction. The construction with sacrificial layers were then placed in an oven heated to 320° C. for eight minutes. Upon removal from the heated oven, the combination was allowed to cool to room temperature. The sacrificial ePTFE material was then removed.

The construction was then removed from the mandrel and another mandrel (1.83 mm diameter×30.5 cm long) inserted into the reinforced end of the construction. With the mandrel supporting the reinforced end, a 5 mm long slit was made proximal to the reinforced portion of the sheath-deployment line construction. A second mandrel was placed inside the construction up to the 5 mm slit where it exited the construction. The proximal portion of the sheath-deployment line construction was converted into a filament by placing the proximal-end into the chucks of the film wrapper chucks and rotating the film wrapper approximately 2,800 times while the mandrel with the reinforced construction was immobilized. After the construction was spun into a filament, the filament was strengthened by briefly applying heat to the filament with a soldering iron set at 450° C. The strengthened filament was smoothed and rendered more uniform in diameter by passing the filament over a 1.8 cm diameter×3.8 cm long dowel heated to approximately 320° C. The filament was passed over the heated dowel at a 45° angle under slight tension. This process was repeated two more times over the entire length of the filament.

The filament portion of the sheath-deployment line of the present invention was routed through a lumen of a primary catheter and connected to a control knob. The control knob was part of a hub located at the proximal end of the primary catheter. When the deployment line portion of the sheath-deployment line was pulled, the sheath portion was retracted from around the stent.

Example 2

This example describes the construction of a deployment system of the present invention. Construction of the system begins with the preparation of a distal catheter shaft for receiving an expandable stent. Once the distal catheter was prepared, the expandable stent was placed within a sheath-deployment line. The distal catheter portion of this combination was attached to a primary catheter shaft. The deployment line portion was then routed through the primary catheter to a control knob. The control knob was part of a hub located proximally on the primary catheter. The sheath portion of the sheath-deployment line was in the form of a double-walled tube.

A tubular material three inches long was obtained from Burnham Polymeric, Inc., Glens Falls, N.Y. for use as the distal catheter shaft. The tube was made of a polyether block amide material, commonly known as PEBAX® resin and reinforced with a stainless steel braid. The outer diameter (OD) was 1.01 mm and the inner diameter (ID) was 0.76 mm. A endo-prosthesis mounting member in the form of a compressible material was then placed on the catheter. To place the endo-prosthesis mounting member on the catheter, the catheter was mounted on a mandrel having an outer diameter of 0.74 mm. A film of porous expanded polytetrafluoroethylene (ePTFE) was obtained according to the teachings in U.S. Pat. No. 5,814,405, issued to Branca, which is incorporated herein by reference. A discontinuous coating of fluorinated ethylene propylene (FEP) was applied to one side of the ePTFE material in accordance with U.S. Pat. No. 6,159,565, issued to Campbell et al., which is incorporated herein by reference. An edge of the ePTFE-FEP composite film two inches wide was attached with heat to the catheter shaft. After initial attachment, the film was wrapped around the catheter shaft forty-five (45) times under light tension. With every fifth wrap of the film, and on the final layer, the film is further attached to itself with heat. This procedure provides a endo-prosthesis mounting member on the distal catheter shaft. The expandable stent is mounted over the endo-prosthesis mounting member. The endo-prosthesis mounting member provides a means of retaining an expandable stent on the catheter shaft during storage, delivery to an implantation site, and deployment of the expandable stent at the implantation site. Optionally, the endo-prosthesis mounting member may be reinforced with a thin coating of an elastomeric material such as silicone, urethane, and/or a fluoroelastomer.

An eight (8) cell, 6 mm diameter, nitinol stent was obtained from Medinol Ltd., Tel-Aviv, Israel. The stent was placed over the endo-prosthesis mounting member of the catheter in an expanded state. The combination was placed within a machine having a mechanical iris that compacts or compresses the stent portion of the assembly onto the endo-prosthesis mounting member. While retained in the mechanical iris machine, the stent was reduced in temperature from room temperature to approximately five degrees centigrade (5° C.). At the reduced temperature, the iris machine was actuated to compact, or collapse, the stent onto the endo-prosthesis mounting member. While in the refrigerated, compressed configuration, the catheter, endo-prosthesis mounting member, and stent were placed within a sheath-deployment line of the present invention.

The sheath-deployment line having a length equal to, or greater than, the length of the final deployment system was made as follows. A stainless steel mandrel measuring 1.73 mm in diameter was covered with a sacrificial layer of ePTFE. The sacrificial ePTFE material aids in removal of the sheath-deployment line from the mandrel. Two wraps of a thin, polytetrafluoroethylene (PTFE) membrane were applied to the mandrel. The ePTFE membrane was applied so the primary strength of the film was oriented parallel with the longitudinal axis of the mandrel. The film was initially tacked in place with heat applied with a soldering iron. The membrane thickness measured about 0.0002" (0.005 mm) and had tensile strengths of about 49,000 psi (about 340 KPa) in a first direction and of about 17,000 psi (about 120 KPa) in a second direction (perpendicular to the first direction). The tensile measurements were performed at 200 mm/min. load rate with a 1" (2.5 cm) jaw spacing. The membrane had a density of about 2.14 g/cm$^3$. The membrane was further modified by the application of an FEP coating on one side in accordance with U.S. Pat. No. 6,159,565, issued to Campbell et al., which is incorporated herein by reference. Next, two wraps of another ePTFE film made according to the teachings of Bacino in U.S. Pat. No. 5,476,589 and further modified with a discontinuous layer of an FEP material applied to one side of the ePTFE film were applied to one end of the construction (approx. 1" wide). U.S. Pat. No. 5,476,589 is incorporated herein by reference. These two wraps had the primary strength direction of the film oriented perpendicular to the mandrel's longitudinal axis. These layers of film provide additional "hoop" or "radial" strength to the sheath-deployment line construct. The mandrel and sheath-deployment line construct were placed in an air convection oven obtained from The Grieve Corporation, Round Lake, Ill., and subjected to a thermal treatment of 320° C. for 12 minutes. After air cooling, the ePTFE/FEP tube construct was removed from the mandrel and the sacrificial ePTFE layer removed. In this example, a length of sheath-deployment line extending beyond the end of the stent was provided. The additional length of sheath-deployment line was folded back over sheath portion enclosing the stent to form a double-walled construct. The double-walled sheath-deployment line had an inner wall and an outer wall. The inner wall was against the stent and the outer wall included the integral deployment line portion of the construct. The construct was then attached to a primary catheter shaft using heat and standard materials.

The deployment line portion of the sheath-deployment line was made by splitting the sheath-deployment line along its length from a proximal end up to, but not including, the sheath portion enclosing the stent. The material thus obtained was gathered into a filament by rolling the material. Heat was applied to the material to set the material in the filamentous form. The deployment line filament was routed through a lumen in the primary catheter and connected to a control knob. The control knob was part of a hub located at the proximal end of the primary catheter. When the deployment line portion of the sheath-deployment line was pulled, the sheath portion was retracted from around the stent.

Example 3

This example describes the incorporation of a means for initiating or maintaining conversion of the sheath portion of the sheath-deployment line to deployment line by introducing perforations and intentional stress risers into the sheath.

The sheath-deployment line from Example 2 is modified as follows. Prior to rolling the sheath portion into a double-walled construct and loading the stent therein, the sheath is perforated and/or supplied with "stress risers" that facilitate in separation of the tubular sheath upon retraction of the deployment line portion. An appropriate laser for making the perforations or stress risers is a 20 watt $CO_2$ laser obtained from Universal Laser Systems, Scottsdale, Ariz. To form the perforations in the sheath portion, the sheath is placed on a sandblasted stainless steel mandrel and exposed to the laser to cut a series of holes in a part of the tube that will subsequently serve as the outer wall of the double-walled construct. The geometry of the holes can be varied depending on the application. The perforated sheath portion is used on a deployment line system of the present invention as described in Example 2. In this example, tension applied to the deployment line portion at the hub end of the catheter results in retraction of the sheath from around the stent and also results in parting the sheath at the perforations. As the sheath portion is separated, the sheath material becomes convertible to deployment line.

Example 4

This example describes the incorporation of a means for initiating or maintaining conversion of the sheath portion of the sheath-deployment line to deployment line by the use of an appropriate splitting means.

The primary catheter from Example 2 is modified as follows. The primary portion of the catheter is provided with a notch in the wall in 180 degrees opposition and slightly distal to the entry point of the deployment line portion into the catheter lumen. The notch is further modified to provide a small cutting edge in the notch. In one embodiment, the cutting edge is simply attached to the notch with heat, adhesives, and the like. In another embodiment, the cutting edge is formed by exposing a portion of a metallic braid used to reinforce the catheter shaft and forming the braid into a cutting edge. In this example, tension applied to the deployment line portion at the hub end of the catheter results in retraction of the sheath from around the stent and also results in parting the sheath at the perforations. As the sheath portion is separated, the sheath material becomes convertible to deployment line.

Example 5

This example describes the construction of a deployment system of the present invention for use in the delivery and deployment of both self-expanding as well as balloon expandable devices. The deployment system of this example utilizes an endo-prosthesis mounting member in the form of an inflatable balloon.

A sheath-deployment line having a length equal to, or greater than, the length of the final deployment system is made as follows. A stainless steel mandrel measuring 1.73 mm in diameter is covered with a sacrificial tube of ePTFE. The sacrificial ePTFE material aids in removal of the sheath-deployment line from the mandrel. Two wraps of a thin, polytetrafluoroethylene (PTFE) membrane is applied to the mandrel. The ePTFE membrane is applied so the primary strength of the film is oriented parallel with the longitudinal axis of the mandrel. The film is initially tacked in place with heat applied with a soldering iron. The membrane thickness measured about 0.0002" (0.005 mm) and had tensile strengths of about 49,000 psi (about 340 KPa) in a first direction and about 17,000 psi (about 120 KPa) in a second direction (perpendicular to the first direction). The tensile measurements are performed at 200 mm/min. load rate with a 1 inch (2.5 cm) jaw spacing. The membrane has a density of about 2.14 $g/cm^3$. The membrane is further modified by the application of a fluorinated ethylene propylene (FEP) coating on one side in accordance with U.S. Pat. No. 6,159,565, issued to Campbell et al. and incorporated herein by reference. Next, two wraps of another ePTFE film made according to the teachings of Bacino in U.S. Pat. No. 5,476,589, which is incorporated herein by reference, and further modified with a discontinuous layer of an FEP material applied to one side of the ePTFE film are applied to one end of the construction (approx. 1" wide). These two wraps have the primary strength direction of the film oriented perpendicular to the mandrel's longitudinal axis. These layers of film provide additional "hoop" or "radial" strength to the sheath-deployment line construct. The mandrel and sheath-deployment line construct are placed in an air convection oven obtained from The Grieve Corporation, Round Lake, Ill., and subjected to a thermal treatment of 320° C. for 12 minutes. After air cooling, the ePTFE/FEP tube construct is removed from the mandrel and the sacrificial ePTFE layer removed. Placement of this construct over an expandable stent and formation of a deployment line portion therefrom is described below.

As seen in FIG. 10, a balloon expandable NIRflex™ stent (14), available from Medinol Ltd, Tel-Aviv, Israel, is placed over and compacted around a deflated and collapsed angioplasty balloon mounted on a delivery catheter shaft (19). The angioplasty balloon is made in accordance with U.S. Pat. No. 5,752,934 to Campbell et al., which is incorporated herein by reference, and available from W. L. Gore & Associates, Inc., Flagstaff, Ariz. under the tradename APTERA® angioplasty balloon. The APTERA® angioplasty balloon serves as an endo-prosthesis mounting member (18a) for receiving and retaining the compacted stent (14).

While the stent is confined in a compacted configuration, a length of sheath-deployment line (12) is placed over the compacted stent and extended beyond the end of the stent. The additional length of sheath-deployment line is folded back over sheath portion enclosing the stent to form a double-walled construction. The double-walled sheath-deployment line has an inner wall and an outer wall. The inner wall is against the stent and the outer wall includes the integral deployment line portion of the construct.

The deployment line portion of the sheath-deployment line is made by splitting the sheath-deployment line along its length from the proximal end toward the distal end for a distance. The slit can range in length from about one centimeter to substantially the entire length of the sheath-deployment line construction up to, but not including, the sheath portion enclosing the stent. It is preferred to form the deployment line portion near the proximal end of the delivery catheter. The material thus obtained is gathered into a filament by rolling the material. Heat is applied to the material to set the material in the filamentous form. The sheath-deployment line is routed through a dedicated lumen in the delivery catheter and exits at a hub where the deployment line portion is attached to a control knob. The control knob is part of a hub located at the proximal end of the primary catheter. When tension is applied to the deployment line portion of the sheath-deployment line, the sheath portion retracts from around the stent. Removal of the sheath portion from the underlying stent frees the stent to expand. The NIRflex™ stent of this example is expanded by inflating the APTERA® angioplasty balloon. Once the stent is expanded, the balloon is deflated and the delivery catheter along with the sheath-deployment line construction removed from the implant recipient. When self-expanding stents are used in the present invention, the balloon is useful as an endo-prosthesis mounting member.

The invention claimed is:

1. A deployment system for an endoluminal device comprising:
   an expandable endoluminal device mounted on a delivery catheter provided with an endo-prosthesis mounting member;
   a removable sheath in the form of a continuous double-walled tube adapted to cover and constrain at least a portion of said endoluminal device in an introductory profile;
   wherein said deployment system includes a deployment line integral with and extending from one wall of said double-walled tube to which tension can be applied to aid endoluminal device deployment;
   wherein upon endoluminal device deployment, said double-walled tube progressively unrolls from around said endoluminal device through actuation of said deployment line to form removed sheath material;
   wherein said removed sheath material begins to become converted to deployment line at a point where said removed sheath material breaks apart, separates, and converges into deployment line material in the form of an elongated filament; and
   wherein said converged deployment line material is removed from said deployment system along with said deployment line.

2. The deployment system of claim 1 wherein said double-walled tube comprises an extruded thin-walled tube.

3. The deployment system of claim 1 wherein said double-walled tube comprises a thin continuous film.

4. The deployment system of claim 1 wherein said double-walled tube is in the form of an extruded thin-walled tube reinforced with a thin continuous film tube.

5. The deployment system of claim 1 wherein the sheath confines an endo-prosthesis mounting member to a smaller profile on the delivery catheter than an endo-prosthesis mounting member without the sheath.

6. The deployment system of claim 1 wherein the sheath comprises a wall with a thickness of less than 0.05 mm.

7. The deployment system of claim 1 wherein the sheath comprises a fluoropolymer.

8. The deployment system of claim 1 wherein one wall of said double-walled tube is placed over the other wall and one wall moves past the other wall upon unrolling of said double-walled tube.

9. The deployment system of claim 1 wherein the system includes a single catheter shaft.

10. The deployment system of claim 9 wherein the catheter shaft extends distally beyond the endoluminal device in its introductory profile.

11. The deployment system of claim 1 wherein actuation of the deployment line is achieved at least in part with an active elastic element incorporated therein.

12. The deployment system of claim 1 further comprising at least a portion of a second catheter co-axially placed over at least a portion of said delivery catheter.

13. The deployment system of claim 12 wherein said at least a portion of a second catheter substantially confines said sheath-deployment line.

14. The deployment system of claim 1 wherein the endo-prosthesis mounting member is in the form of an inflatable balloon.

15. The deployment system of claim 14 wherein the inflatable balloon includes polytetrafluoroethylene.

16. The deployment system of claim 1 wherein the endoprosthesis mounting member is non-inflatable.

17. The deployment system of claim 1 wherein the length of sheath retracted from the expandable endoluminal device is essentially half the length of deployment line displaced during deployment of the expandable endoluminal device.

18. The deployment system of claim 1 wherein the sheath is not attached to a catheter shaft.

19. A deployment system for an endoluminal device comprising:
   an expandable endoluminal device placed over an endo-prosthesis mounting member and at least partially enclosed by a removable sheath;
   wherein said removable sheath comprises a polymeric material in the form of a continuous double thin-walled tube adapted to surround at least a portion of the expandable endoluminal device and constrain the expandable endoluminal device in an introductory profile on the endo-prosthesis mounting member;
   an extension of the double thin-walled tube in the form of a filamentous deployment line, wherein the deployment line extension is integral and continuous with the double thin-walled tube; and
   wherein upon actuation of the deployment line, the double thin-walled tube unrolls from the endoluminal device and converts from the double thin-walled tube to form to a single elongated deployment line filament.

20. The deployment system of claim 19 wherein said double-walled tube comprises an extruded thin-walled tube.

21. The deployment system of claim 19 wherein wherein said double-walled tube comprises a thin continuous film.

22. The deployment system of claim 19 wherein said double-walled tube is in the form of an extruded thin-walled tube reinforced with a thin continuous film tube.

23. The deployment system of claim 19 wherein the sheath confines an endo-prosthesis mounting member to a smaller profile on the delivery catheter than an endo-prosthesis mounting member without the sheath.

24. The deployment system of claim 19 wherein the sheath comprises an extruded fluoropolymer tube.

25. The deployment system of claim 19 wherein the sheath is convertible to deployment line over at least a portion of the sheath length.

26. The deployment system of claim 19 further comprising a catheter placed within the endo-prosthesis mounting member.

27. The deployment system of claim 19 wherein the endo-prosthesis mounting member is in the form of an inflatable balloon.

28. The deployment system of claim 27 wherein the inflatable balloon includes polytetrafluoroethylene.

29. The deployment system of claim 19 wherein the endo-prosthesis mounting member is non-inflatable.

30. The deployment system of claim 26 wherein the catheter has a single lumen.

31. The deployment system of claim 19 further comprising at least a portion of a second catheter co-axially placed over at least a portion of said delivery catheter.

32. The deployment system of claim 31 wherein said at least a portion of a second catheter substantially confines said sheath-deployment line.

33. The deployment system of claim 19 wherein the polymeric material includes a fluoropolymer.

34. The deployment system of claim 33 wherein the fluoropolymer is polytetrafluoroethylene.

35. The deployment system of claim 34 wherein the polytetrafluoroethylene is porous expanded polytetrafluoroethylene.

36. The deployment system of claim 35 wherein the tube has a wall with a thickness of less than 0.05 mm.

37. The deployment system of claim 19 wherein a first portion of the removable sheath substantially surrounds at least a portion of the expandable endoluminal device and a second portion of the removable sheath substantially covers the first portion.

38. The deployment system of claim 37 wherein the deployment line is integral with the second portion of the removable sheath.

39. The deployment system of claim 19 wherein the sheath is not attached to a catheter shaft.

* * * * *